United States Patent [19]

Vletter

[11] Patent Number: Plant 7,379

[45] Date of Patent: Nov. 13, 1990

[54] LILY PLANT NAMED MONA LISA

[75] Inventor: Floris Vletter, Rijnsburg, Netherlands

[73] Assignee: Gebr. Vletter & J. A. Den Haan, Netherlands

[21] Appl. No.: 373,336

[22] Filed: Jun. 29, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A lily plant named Mona Lisa principally characterized by its variegated flower color, with the petals being a generally mid-pink in the center, white along the edges and rebent tip, and a deep pink-red near its base and along the mid vein, with spot markings of similar color.

1 Drawing Sheet

The present invention comprises a new and distinct cultivar of lily, botanically known as lilium (Oriental hybrid) and hereinafter referred to by the cultivar name Mona Lisa.

Mona Lisa is a product of a planned breeding program, which had the primary objective of creating new lily cultivars with a new orange color, while retaining the desired characteristics of the parent cultivars.

Mona Lisa was originated from a hybridization made by the inventor Floris Vletter from a hybridization made in a controlled breeding program in Rijnsburg, The Netherlands in 1979. The female parent was a cultivar designated F 4431-77. The male parent of Mona Lisa was the cultivar Stargazer.

Mona Lisa was discovered and selected as one flowering plant within the progeny of the stated cross by the inventor on June 22, 1982 in a controlled environment in Rijnsburg, The Netherlands.

The first act of asexual reproduction of Mona Lisa was accomplished when scales were taken by the inventor from the initial selection on Aug. 22, 1982 in a controlled environment in Rijnsburg, The Netherlands. Horticultural examination of selected units initiated Oct. 17, 1985 has demonstrated that the combination of characteristics as herein disclosed for Mona Lisa are firmly fixed and are retained through successive generations of asexual reproduction.

Mona Lisa has not been observed under all possible environmental conditions. The phenotype may vary significantly with variations in environment such as temperature, light intensity, and day length. The following observations, measurements, and comparisons describe plants grown in Wageningen, The Netherlands under greenhouse conditions which approximate those generally used in commercial practice.

Mona Lisa is distinguished primarily by its medium pink flower color, with white edges and tips. The mid-vein, spot markings, and base areas of the petals are a deeper pinkish red. The flowers are medium to long and wide to very wide, with the petal types being substantially rebent.

The accompanying photographic drawing shows in top perspective view typical flower and foliage characteristics of Mona Lisa, with colors being as true as possible with illustrations of this type.

In the following description, color references are made to The Royal Horticultural Society Colour Chart.

Origin: Breeding program.

Parentage:

*Male parent.*—Stargazer.

*Female parent.*—F 4431-77.

Classification:

*Botanic.*—Lilium.

*Commercial.*—Oriental hybrid.

The Plant

Form: Typical.

Height: Relatively short, approximately 50 cm measured from the opening of the anthers of the first flower.

Growth habit: Excellent grower.

Stalk:

*Anthocyanin coloring.*—Present, strong at base.

*Color.*—Light green.

*Growth of hair.*—Present.

*Type of coat of hair.*—Long.

*Division of coat of hair.*—Primarily in leaf axils.

*Internode length.*—Uniform.

*Cross section.*—Round.

*Bulbils.*—Absent.

Leaf:

*Position.*—Spread out.

*Top angle of the base with the stalk.*—Sharp, 30°-45°.

*Length.*—Short.

*Width.*—Wide to very wide.

*Form (middle third part of the stalk).*—Elliptical.

*Color of the top.*—Mid-green.

*Lustre of the top.*—Middle.

*Growth of hair at the bottom.*—Absent.

*Tip.*—Pointed.

*Curve of the edge.*—Present.

*Membraneous edge.*—Absent.

*Indentation of the edge.*—Absent.

*Uniformity.*—Present.

*Form in crosssection.*—Flat.

*Top part.*—Weakly bent back.

*Flexibility.*—Strong.

Flower structure:

*Type.*—Umbel raceme.

*Secondary flowers.*—Absent.

*Growth of hair.*—Present.

*Bracts.*—Present.

*Number of bracts in comparison with the number of primary flowers.*—Even.

*Bracteoles.*—Present.

*Number of bracteoles in comparison with the total number of flowers.*—Equal.

Flowers:

*Position.*—Erect, but inclining slightly horizontally.

*Type.*—Bowl-shaped.

*Cross-section.*—Middle to large.

*Length of longest flower stalk.*—Short.

*Length of longest exterior petal.*—Medium to long.

*Width of widest exterior petal.*—Wide to very wide.

*Length of longest interior petal.*—Medium to long.

*Width of widest interior petal.*—Wide to very wide.

*Color of the inside and outside of the interior petals.*—Center pink 55C, gradually fading at the tip and edges to 155D, with spot markings and main vein red 47A-B.

*Color of the inside and outside of the exterior petals.*—Center pink 55C, tip and edges 155D, with spot markings, base, and main vein red 47A-B.

*Type of spot markings on the inside.*—Smudge type markings, elliptical, 1-2 mm long.

*Density of the spots in the marking.*—Fairly dense and conspicuous on pink central upper petal portions; less dense and conspicuous on lower petals.

*Color of the inside and outside of the throat.*—Green surrounded by yellow.

*Surface structure of the inside of the throat.*—Papillate.

*Lustre at the inside.*—Present, but very weak.

*Curve of the edges.*—Present.

*Type of curve of the edge of the petals.*—Mildly undulating.

*Flexure of petals.*—Present.

*Bended part of the petals.*—Only at tip.

*Extent of bending.*—Non-uniform variously weak to average.

*Length of stamens.*—Average.

*Color of the filaments.*—White.

*Color of the anthers.*—Purplish brown.

*Color of the pollen.*—Dark brown.

*Length of the pistil.*—Average.

*Color of the style.*—Light green.

*Color of the stigma.*—Purple.

*Fragrance.*—Present, strong.

Bulb:

*Type, (dormant).*—Type. 2.

*Tip.*—Pointed.

*Density of scales.*—Close.

*Tip of the scales.*—Pointed.

*Color of the exterior scales.*—White/purple.

I claim:

1. A new and distinct cultivar of lily plant named Mona Lisa, as illustrated and described.

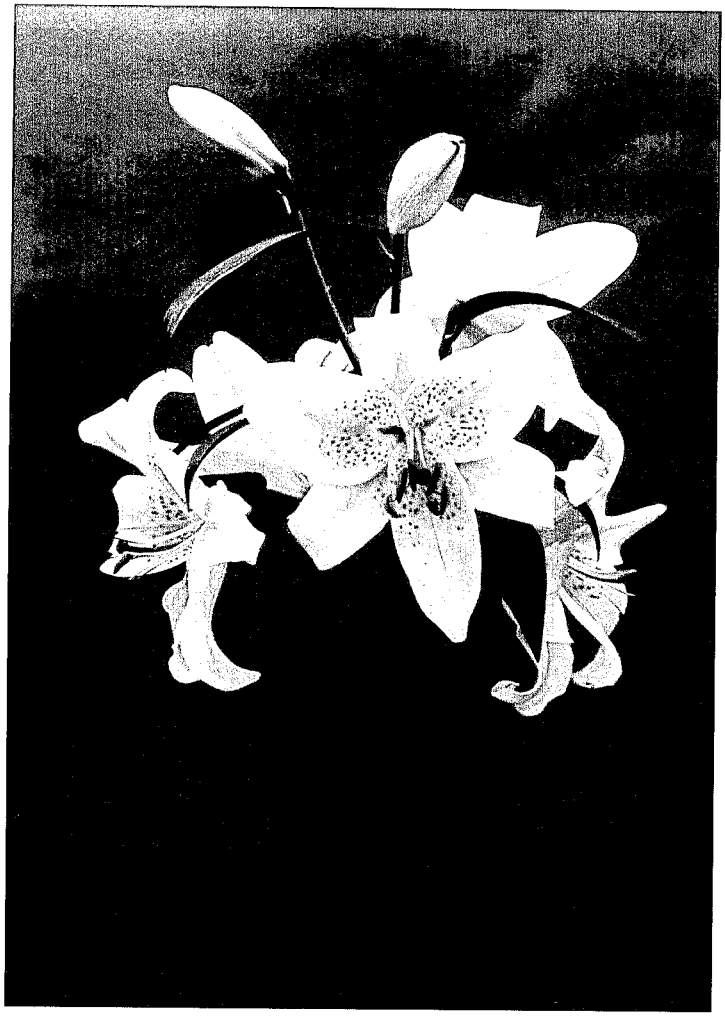

* * * * *